United States Patent [19]

Wilharm et al.

[11] Patent Number: 4,996,301

[45] Date of Patent: Feb. 26, 1991

[54] POLYFUNCTIONAL α-DIAZO-β-KETO ESTERS AND THEIR USE IN LIGHT-SENSITIVE COMPOSITIONS

[75] Inventors: Peter Wilharm, Wiesbaden; Hans-Joachim Merrem, Seeheim-Jugenheim; Georg Pawlowski, Wiesbaden, all of Fed. Rep. of Germany

[73] Assignee: Hoechst Aktiengesellschaft, Frankfurt am Main, Fed. Rep. of Germany

[21] Appl. No.: 464,003

[22] Filed: Jan. 12, 1990

[30] Foreign Application Priority Data

Jan. 12, 1989 [DE] Fed. Rep. of Germany ....... 3900735

[51] Int. Cl.$^5$ ................. C07C 245/18; C07C 245/14; C07F 5/02
[52] U.S. Cl. .................................... 534/556; 534/558; 534/560; 534/561; 534/564; 534/565; 549/274; 560/29; 560/60; 560/126; 560/174; 564/48; 252/501.1; 430/170; 430/189
[58] Field of Search ................................ 534/556–565

[56] References Cited

U.S. PATENT DOCUMENTS

| 3,226,381 | 12/1965 | Breslow et al. | 534/561 |
| 4,163,106 | 7/1979 | Kondo et al. | 560/9 X |
| 4,339,522 | 7/1982 | Balanson et al. | 430/192 |
| 4,622,283 | 11/1986 | Gray | 430/191 |
| 4,626,491 | 12/1986 | Gray | 534/556 X |
| 4,735,885 | 4/1988 | Hopf et al. | 430/192 |

FOREIGN PATENT DOCUMENTS

| 0129694 | 1/1985 | European Pat. Off. | 534/556 |
| 0195986 | 10/1986 | European Pat. Off. | 534/556 |
| 0198674 | 10/1986 | European Pat. Off. | 534/556 |
| 0262864 | 4/1988 | European Pat. Off. | 534/556 |
| 3841571 | 6/1989 | Fed. Rep. of Germany | 534/564 |

OTHER PUBLICATIONS

Willson et al., "New Diazoketone Dissolution Inhibitors for Deep U.V. Photolithography", Advances in Resist Technology and Processing IV, Mar. 2≧3, 1987, pp. 2–10.
Sugiyama et al., "Positive Excimer Laser Resists Prepared with Aliphatic Diazoketones", SPIE Proc., 920, 51, 1988, pp. 51–61.
Korobitsyna et al., Chemical Abstracts, vol. 99, No. 53746y (1983).
Sugyama et al., Chemical Abstracts, vol. 112, No. 28233h (1990).
Sugyama et al., Chemical Abstracts, vol. 111, No. 123850v (1989).
Abstract of JP 51-128906.
Sugiyama et al., Chemical Abstracts, vol. 111. No. 164016w (1989).
Hendrickson et al., Journal of Organic Chemistry, 33, 3610(1968).

Primary Examiner—Floyd D. Higel
Assistant Examiner—Fiona T. Powers
Attorney, Agent, or Firm—Foley & Lardner, Schwartz, Jeffery, Schwaab, Mack, Blumenthal & Evans

[57] ABSTRACT

Polyfunctional α-diazo-β-keto esters of the general formula I are described

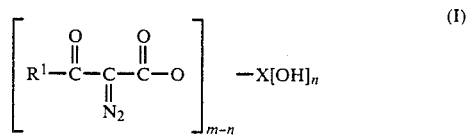

in which
$R^1$ denotes an aliphatic, cycloaliphatic or araliphatic or aromatic radical having 4 to 20 carbon atoms, in which individual $CH_2$ groups can be replaced by oxygen or sulfur atoms or by N— or NH groups and/or contain keto groups,
X denotes an aliphatic, cycloaliphatic, carbocyclic, heterocyclic or araliphatic radical having 2 to 22 carbon atoms, in which individual $CH_2$ groups can be replaced by oxygen or sulfur atoms or by the groups $-NR^2-$, $-C(O)-O-$, $-C(O)-NR^2-$, $-C(O)-N-$,
$\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;|$ $-NR^2-C(O)-NR^3-$, $-O-C(O)-NR^2-$, $-O-C(O)-N-$ or $-O-C(O)-O-$ or
$\;\;\;\;\;\;\;\;\;\;\;\;\;\;|$ CH groups can be replaced by $-N-$,
$\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;|$ in which $R^2$ and $R^3$ independently of one another represent hydrogen or an aliphatic, carbocyclic or araliphatic radical,
m denotes an integer from 2 to 10 and
n denotes an integer from 0 to 2,
wherein
m−n is ≧2.

The compounds mentioned are used as photoactive components in radiation-sensitive mixtures.

30 Claims, No Drawings

POLYFUNCTIONAL α-DIAZO-β-KETO ESTERS AND THEIR USE IN LIGHT-SENSITIVE COMPOSITIONS

BACKGROUND OF THE INVENTION

The invention relates to new polyfunctional α-diazo-β-keto esters, a process for their preparation and their use as photoactive components in radiation-sensitive mixtures.

Radiation-sensitive mixtures which contain photoactive diazo derivatives and are suitable for irradiation with high-energy UV radiation have been described in the literature for some time.

Positively operating radiation-sensitive mixtures which contain a diazo derivative of Meldrum's acid as the photoactive compound are mentioned in U.S. Pat. No. 4,339,522. This compound is said to be suitable for exposure to high-energy UV radiation in the range from 200 to 300 nm. However, it has been found that when these mixtures are used, the photoactive compound is exudated under the relatively high processing temperatures frequently employed in practice; the radiation-sensitive mixture loses its original activity, so that reproducible structurings are not possible.

EP-A-0,198,674 and 0,262,864, U.S. Pat. No. 4,622,283 and SU-A-1,004,359 provide 2-diazo-cyclohexane-1,3-dione or -cyclopentane-1,3-dione derivatives as photoactive compounds for radiation-sensitive mixtures of the type described. These compounds have a lower volatility, but instead, depending on the substitution pattern present, exhibit a poor compatibility in the radiation-sensitive mixture. This manifests itself in particular by crystallization of the photoactive compound during drying of the layers, by insolubility thereof in solvents used in practice or by a layer inhomogeneity caused by phase separation.

Other positively operating photoactive compounds which are sensitive in the low UV range are known from EP-A-0,129,694 and U.S. Pat. No. 4,735,885. The compounds described in these documents have the disadvantage that the carbenes formed from them during exposure do not have a stability in the matrix which is adequate for the desired carboxylic acid formation. This leads to an inadequate solubility difference between the exposed and nonexposed areas in the developer and therefore to an undesirably high removal rate of the non-exposed areas. A possible explanation for this phenomenon is given by C. G. Willson et al. in SPIE Vol. 771, "Advances in Resist Technology and Processing IV", 2 (1987).

EP-A-0,195,986 therefore proposes α-phosphoryl-substituted diazocarbonyl compounds as photoactive compounds, since these have an increased carbene stability. In practice, however, such compounds probably find only minor use, since atoms which can potentially be used as doping agents, such as, for example, the phosphorus contained in these compounds, must be very meticulously excluded during the processing processes.

In their paper "Positive Excimer Laser Resist Prepared with Aliphatic Diazoketones" (SPIE Proc., 920, 51 (1988)), H. Sugiyama, E. Ebata, A. Mizushima and K. Nate introduce novel α-diazoacetoacetates which are employed as photoactive compounds in positively operating radiation-sensitive mixtures, in particular for use with radiation in the low UV range. Since these are derivatives of aceto-acetic acid, the keto group in the β-position relative to the ester group is directly adjacent to a terminal methyl group. Radiation-sensitive mixtures which contain the compounds mentioned as photoactive components exhibit good bleaching properties, but their properties in respect of image differentiation are poor.

SUMMARY OF THE INVENTION

Accordingly, it is an object of the present invention to provide a photoactive compound of high sensitivity in the UV range, which does not have the numerous disadvantages described and which allows good differentiation between the exposed and non-exposed layer areas.

Another object of the present invention is to provide a photoactive compound which is readily compatible with the most diverse polymers which can be used in practice, and which is not exuded from the radiation-sensitive mixture so formed.

An additional object of the present invention is to provide a photoactive compound which has a high thermal stability as well as a photosensitivity which meets the requirements in practice.

A further object of the present invention is to provide a process for producing the foregoing compound.

In accomplishing the foregoing objectives, there has been provided, in accordance with one aspect of the present invention, a polyfunctional α-diazo-β-keto ester of the general formula I

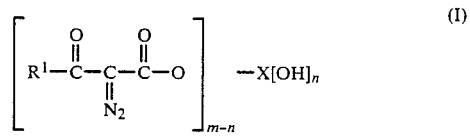

in which
R$^1$ denotes an aliphatic, cycloaliphatic or araliphatic or aromatic radical having 4 to 20 carbon atoms, in which individual CH$_2$ groups can be replaced by oxygen or sulfur atoms or by N- or NH groups and/or contain keto groups, X denotes an aliphatic, cycloaliphatic, carbocyclic, heterocyclic or araliphatic radical having 2 to 22 carbon atoms, in which individual CH$_2$ groups can be replaced by oxygen or sulphur atoms or by the groups

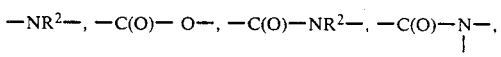

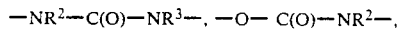

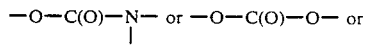

CH groups can be replaced by —N—, in which R$^2$ and R$^3$ independently of one another represent hydrogen or an aliphatic, carbocyclic or araliphatic radical,
m denotes an integer from 2 to 10 and
n denotes an integer from 0 to 2,
wherein
m−n is ≧2.

In accordance with another aspect of the present invention there is provided a process for the preparation of the foregoing compound which comprises the steps of dissolving a β-keto ester of the general formula II

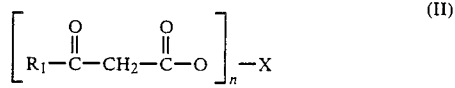 (II)

in about a 5- to 50-fold amount of a suitable solvent and reacting this solution with about a 1- to 1.3-fold excess of a diazo transfer reagent and a base, preferably a tertiary amine, freeing the reaction mixture of excess reagents and solvents, taking up the residue in a water-immiscible solvent, washing the solution with potassium hydroxide solution and then with water until neutral, and isolating the product after drying over a suitable drying agent.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

In the preferred embodiment, $R_2$ and $R_3$ denote hydrogen, $(C_1-C_3)$alkyl, $(C_6-C_{12})$aryl or $(C_6-C_{11})$aralkyl, in which the radicals - in particular aryl or aralkyl - can likewise be substituted on the nucleus by alkyl, alkoxy, halogen or amino. $R_2$ and $R_3$ particularly preferably represent hydrogen or $(C_1-C_3)$alkyl, but in particular hydrogen.

The radicals $R^1$ and X can be optionally substituted, in particular by $(C_1-C_3)$alkyl $(C_1-C_3)$alkoxy, halogen, amino or nitro. Radicals $R^1$ and X which are substituted by $(C_1-C_3)$alkyl or $(C_1-C_3)$alkoxy are preferred. In particular, if $R^1$ and X represent an alkyl radical the unsubstituted derivatives are preferred.

The aliphatic radicals $R^1$ can be either straight-chain or branched. The number of chain members here is preferably 4 to 10, in particular 4 to 8. These include the particularly preferred pure carbon chains and also the substituted chains in which up to 3 $CH_2$ groups are replaced by oxygen atoms or —NH— groups and/or contain keto groups which includes ether, keto, ester, amido or imido groups, that is to say also esters of carbamic acid. In the pure aliphatic radicals $R^1$, ether groups particularly preferably occur twice per radical $R^1$. If the chains are pure, in particular straight-chain, carbon chains, limitation of the number of carbons is not essential; it is entirely possible to employ aliphatic radicals having up to 20 carbon atoms. Nevertheless, the t-butyl radical is preferred.

If $R^1$ denotes a cycloaliphatic radical, the number of ring members is preferably 4, 5, 6 or 12, in particular 4, 5 or 6. The unsubstituted variants are particularly preferred. Examples are the cyclobutyl, cyclopentyl and cyclohexyl radical. The cyclohexyl radical is particularly preferred.

If $R^1$ is an araliphatic radical, the number of members of the aliphatic part is 2 to 11, in particular 2 to 5. If the carbon chain in the aliphatic part is a pure carbon chain, the number of C atoms is preferably 1 or 2. If $CH_2$ groups are replaced by oxygen atoms, these can occur as a bridge member between the aromatic and aliphatic part of the radical $R^1$, and also in the aliphatic part. In both cases, it is particularly preferable for the remaining total number of carbon atoms as chain members in the aliphatic part of this radical to be 1 or 2, the ether oxygen atom being positioned in the case of 2 carbon atoms as chain members such that it is adjacent to both $CH_2$ groups. Amongst these there may be mentioned the benzyl, the phenoxymethylene and the benzyloxymethylene radical. If still further $CH_2$ groups in the aliphatic part of the araliphatic radical $R^1$ are additionally replaced by hetero atoms and/or substitutions are undertaken on these, the total number of chain members of the aliphatic part is 2 to 5, wherein up to 3 chain members are substituted by hetero atoms. This includes, inter alia, phenyl or benzyl radicals bonded via ester groups, but also the benzyl or phenyl esters of carbamic acid. However, the aliphatic part can also be the imido group of an aromatic dicarboxylic acid. The aromatic part of such a radical consists, in particular, of 6 carbon atoms. If the aromatic part of the araliphatic radical is directly adjacent to the keto group, that is to say is bonded as an arylene radical, there are no limitations in respect of the minimum number of carbon atoms present for the aliphatic part occurring therein.

The aromatic radicals $R^1$ preferably contain no hetero atoms, such as, for example, oxygen, in their ring system. If $R^1$ is an aromatic radical, it preferably contains 6 to 12 carbon atoms, in particular 6 carbon atoms, that is to say corresponds to a phenyl radical. However, aromatic radicals $R^1$ are not preferred.

Overall, t-butyl, n-hexyl, nonyl, octadecyl, 2,5-dioxahexyl, cyclopentyl, cyclohexyl, benzyl, phenoxymethyl and benzyloxymethyl may be mentioned as particularly preferred radicals $R^1$. The t-butyl, phenoxymethyl and cyclohexyl radical are particularly preferred.

X represents an aliphatic or cycloaliphatic radical which can be saturated or unsaturated, or a carbocyclic, heterocyclic or araliphatic radical having 2 to 22 carbon atoms, in particular 2 to 17 carbon atoms. In addition, at least one $CH_2$ group in these radicals can be replaced by hetero atoms, such as oxygen or sulfur, or by groups such as

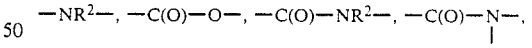

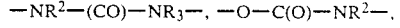

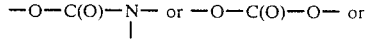

CH groups can be replaced by —N—.

Those variants in which not more than two $CH_2$ groups have been replaced by one type of the above-mentioned groups are particularly preferred in the aliphatic or araliphatic radicals. If $CH_2$ groups are replaced by hetero atoms, the number of these can preferably be not more than 5, in particular not more than 3. It is particularly preferable in this case if all the $CH_2$ groups to be replaced are replaced by hetero atoms of one type.

If the radical X is an unsubstituted saturated or unsaturated aliphatic radical, in the preferred variant this contains not more than 6 carbon atoms. Unsaturated aliphatic radicals X include, in particular, those in which the CH$_2$ or CH groups are not replaced by hetero atoms or the above-mentioned groups. In their particular embodiment, they contain not more than one C—C multiple bond; the number of chain members in such a radical is particularly preferably 4. The radicals X mentioned can be either di- or trivalent, but it is preferable for X to be divalent.

If CH$_2$ groups in the aliphatic radicals X are replaced by hetero atoms, these are preferably bonded in alkylene radicals having in each case at least 2 CH$_2$ groups. If sulfur is the hetero atom in the aliphatic radical X, this particularly preferably occurs only once per radical It is surrounded in particular by alkyl radicals having in each case not more than 3 CH$_2$ groups. If oxygen is employed as the hetero atom in the aliphatic radical, this can occur more frequently per radical, in particular 2 to 4 times. In this case, the alkylene radicals into which two oxygen atoms are bonded contain at least three CH$_2$ groups.

If the number of carbon atoms in the unsubstituted aliphatic radical is greater than 3, this alkylene radical is, in particular, in the form of the branched isomer. The t-butyl or t-pentyl radical is particularly preferred.

In the radical X, it is also possible for several alkyl radicals, in particular the t-butyl or t-pentyl radical, to be bonded via groups, which are mentioned above, which replace hetero atoms or CH$_2$ groups. This is particularly preferable if these radicals are more than divalent.

If the t-butyl or t-pentyl radicals are trivalent, m is at least 3. The value m=4 is preferably achieved by a divalent t-pentyl or t-butyl radical being present twice in the radical X. The value m=4 is also achieved by a divalent propyl radical occurring twice on the radical X.

The value m=6 is preferably achieved by two trivalent radicals (t-butyl or t-pentyl) or three divalent propyl radicals being present in the radical X. The value m=8 is achieved, for example, by the combination of 4 divalent radicals or 2 trivalent radicals with one divalent radical.

A radical X which is more than divalent can also be achieved by the radical containing hetero atoms which are more than divalent: if a CH group is replaced by

m values of 2 to 3 can be achieved If two CH groups are replaced by

m can reach a maximum of 4; if this is a part of a cycloaliphatic ring, m is not more than 2.

In all cases where CH groups in the radical X are replaced by

no replacement of a CH$_2$ group by a further hetero or by one of the groups described above preferably takes place. The number of CH$_2$ groups which lie between the oxygen hetero atom and the radical bonded to the radical X, according to the general formula I, is at least 2; this is particularly the number 2.

Pure cycloaliphatic radicals, that is to say unsubstituted radicals, as a variant of the radical X are not preferred. The cyclohexyl radical is mentioned in particular as the cycloaliphatic radical. However, this can be substituted, in particular by hydroxyl and/or alkyl or alkylene, the valency thereof (that is to say m) preferably being determined by the number of alkylene substituents on the cycloaliphatic radical. A cyclohexyl radical which contains four methylene groups as substituents, which at the same time ensures bonding of the α-diazo-β-keto ester units, in accordance with the general formula I (m=4) is especially preferred. It is particularly preferred for this radical X also to contain a hydroxyl group, in particular a secondary hydroxyl group, so that n=1.

The cycloaliphatic radicals as variants of the radical X are usually rather a combination of a cycloaliphatic and a chain-like aliphatic part. In this case, the cycloaliphatic part is preferably not substituted such that CH$_2$ groups from this part are replaced by hetero atoms or by groups from the above-mentioned series.

An exception is a six-membered ring (heterocyclic radical) of three carboxylic acid amide units in which the coupling of the α-diazo-β-keto ester units of the general formula I is via ethylene groups to the amido nitrogen. In this case m is therefore 3 and n is 0.

However, if X is a combination of a pure cycloaliphatic part and one or more chain-like aliphatic parts having 2 or more carbon atoms, the cycloaliphatic part is, in particular, directly adjacent to a CH$_2$ group which is replaced by one of the above-mentioned hetero atoms or groups. Those variants in which the cycloaliphatic part is directly adjacent to a nitrogen atom, in particular to the

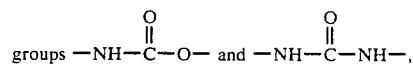

are particularly preferred. In this case, a cyclohexyl radical is preferably employed as the cycloaliphatic part and can be either monovalent or divalent, the latter preferably being in the 1,4-position. In both cases, linking of one of the free valencies of the

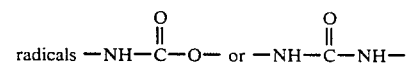

with the α-diazo-β-keto ester unit in accordance with the general formula I is via an alkylene radical having at least 2 CH$_2$ units. If the radical is a

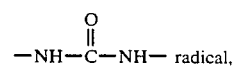 radical, a t-butylene radical is preferably formulated as the linking group. If the radical is a

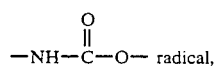
—NH—C(=O)—O— radical, that is to say the linking in question is via the oxygen atom of this group, an ethylene radical is preferably employed as the linking group.

If the variant of group X is an araliphatic radical, the aromatic part, in particular a phenyl or, if divalency exists, a phenylene radical, can be bonded both via a nitrogen atom and via an oxygen atom. However, here also—if both atoms are available—the nitrogen atom is preferred. An example in which the aromatic part is bonded directly via an oxygen atom is an ether oxygen atom bonded via an ethylene group to the α-diazo-β-keto ester unit. A third variant in this case is also the possibility that the aromatic radical, especially if it is monovalent, is bonded via the keto group of a

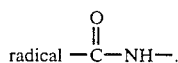
radical —C(=O)—NH—.

In this case, the nitrogen atom carries, in particular, an ethylene radical.

If an araliphatic radical X is present, the aliphatic part of the radical X which is bonded via the nitrogen atom of a

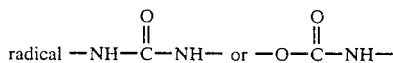
radical —NH—C(=O)—NH— or —O—C(=O)—NH— replacing a CH$_2$ group is in particular a t-butylene or an ethylene radical; if the aliphatic part is bonded via the oxygen atom, this is particularly preferably an ethylene radical.

The fact that an ethylene group is preferably bonded via the oxygen atom of the above-mentioned groups which are to replace a CH$_2$ group in the radical X can also be applied in general to aliphatic radicals, whereas both ethylene radicals and higher aliphatic radicals, in particular of hydrocarbon chains having more than 3 carbon atoms, are bonded via the nitrogen atom. The t-butylene radical is preferred.

If the radicals X are araliphatic and aliphatic, preferably not more than 2 CH$_2$ groups are replaced by radicals such as

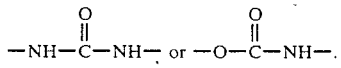
—NH—C(=O)—NH— or —O—C(=O)—NH—.

In the particularly preferred embodiment, the

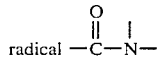
radical —C(=O)—N— as a replacement for a CH group is present only once in a radical X.

In the variants described above for radicals R$^1$ and X, m is preferably an integer from 2 to 8 and n an integer from 0 to 2.

Particularly preferably, m is an integer from to 6 and n=0.

The α-diazo-β-keto esters according to the invention of the general formula I characterized in more detail above are outstandingly suitable as photoactive components in a radiation-sensitive mixture. In particular, the compounds according to the invention are suitable for exposure to radiation of a wavelength of about 190 to 350 nm, preferably 200 to 300 nm. The use of the new polyfunctional compounds as photoactive components in radiation-sensitive mixtures for the preparation of photo-resists of high resolution for microlithography is described in German patent application P 3,900,736.7, filed at the same time and corresponding to co-pending U.S. application No. 07/466,007.

The invention also relates to a process for the preparation of the α-diazo-β-keto esters according to the invention. In this process, it has proved particularly advantageous first to synthesize suitable precursors for β-keto esters of the general formula II and to convert these into the α-diazo-β-keto esters of the formula I by a so-called diazo transfer in a subsequent reaction (compare M. Regitz et al., Org. Prep. Proced., 1, 99 (1969)):

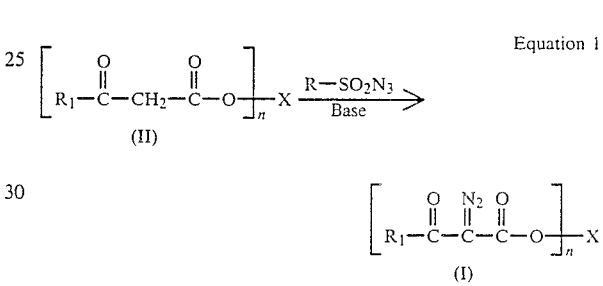

Equation 1

For this purpose, a β-keto ester of the general formula II (in which R$_1$ and X have the meaning given in formula I) are dissolved in about 5 to 50 times, preferably 10 times, the amount (based on the mixture) of a suitable solvent and the solution is cooled to a temperature between about −15° C. and +15° C., preferably between −5° C. and +5° C. Suitable solvents are alcohols, such as methanol and ethanol, alcohol ethers, such as ethylene glycol monomethyl ether, chlorinated hydrocarbons, such as methylene chloride or chloroform, or, preferably, aliphatic nitriles, such as acetonitrile, or mixtures of these solvents. Those which have a boiling point between about 30° C. and 140° C. are particularly preferred here. The actual reaction according to the invention can be carried out by 3 variants.

Variant A:

An about 1- to 1.3-fold excess (based on the number of activated methylene groups to be reacted) of a diazo transfer reagent is added to the cooled solution. Aromatic and aliphatic sulfonyl azides, such as toluenesulfonyl azide, 4-carboxyphenylsulfonyl azide, 2-naphthalenesulfonyl azide or methylsulfonyl azide, have proved to be particularly suitable transfer reagents. The equimolar amount, based on the sulfonyl azide, of a base, preferably a tertiary amine, is then added to the solution. The temperature of the mixture must be kept constant here. Examples of preferred amines are triethylamine, triisopropylamine and diazabicyclo[2.2.2]octane. The use of triethylamine as the base is particularly preferred. The resulting mixture is stirred at the given temperature for about 5 to 50 minutes, preferably 10 to 15 minutes, warmed to room temperature and stirred at this temperature for a further about 1 to 24 hours, preferably 2 to 4 hours. The sulfonamide thereby formed may precipitate, depending on the nature of the sulfonyl azide employed, so that it is filtered off, if appropriate, when the reaction has ended.

Variant B:

Alternatively to variant A, the β-keto ester of the general formula II and the amine can be initially introduced into the reaction vessel under the conditions described above and the sulfonyl azide can then be metered in, while maintaining the temperature.

Variant C:

However, it has proved to be particularly advantageous to use a modified variant A, in which only about a 0.7- to 0.9-fold excess (based on the number of activated methylene groups to be reacted) of a sulfonyl azide, preferably toluenesulfonyl azide, is added to the solution of the β-keto ester of the general formula II and the total amount of the amine is added, while maintaining the given temperature. The mixture is then stirred, if appropriate while warming to room temperature. After about 10-120 minutes, the toluenesulfonyl azide can no longer be detected by chromatography. The mixture is then cooled again, if appropriate, and about a 0.6- to 0.1-fold excess of 4-carboxyphenylsulfonyl azide is this time added, so that a total excess of sulfonyl azide corresponding to variant A results. The crude products prepared by this variant have a high purity.

The mixture obtained according to variants A to C is freed from the solvent and excess reagents and taken up in an inert water-immiscible solvent, in particular methylene chloride or diethyl ether. The mixture is washed twice with 5% strength potassium hydroxide solution to remove sulfonylamide residues and then washed neutral with water, dried over a suitable desiccant and freed from the solvent again. The residue which remains, which, especially if variant C is used, consists almost exclusively of pure α-diazo-β-keto ester of the general formula I, can be worked up by known methods, for example by means of crystallization or chromatography.

The preparation of the β-keto esters of the general formula II required for conversion into the α-diazo-β-keto esters of the general formula I according to the invention can be carried out by various procedures which are known in the literature:

1. In accordance with equation 2, a monofunctional 5-acyl-2,2-dialkyl-1,3-dioxane-4,6-dione (5-acyl-Meldrum's acid) of the general formula III is reacted with a polyhydric alcohol of the general formula IV to give the polyfunctional β-keto ester of the general formula II. The preparation of 5-acyl-Meldrum's acid derivatives of the general formula III and reaction thereof to give β-keto esters of the general formula II is known for monofunctional compounds and can be carried out, for example, analogously to the procedure of Y. Oikawa et al., J. Org. Chem., 43, 2087 (1987) by reaction of acid chlorides with Meldrum's acid, or analogously to the procedure of P. Houghton and D. J. Lapham, Synthesis, 1982, 451 et seq. The products are isolated in their enol form.

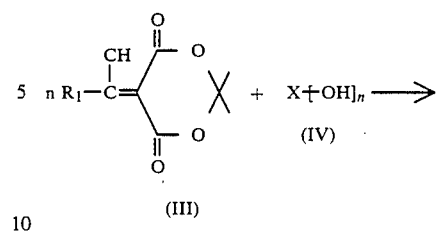

Equation 2

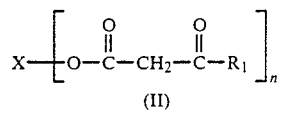

2. In accordance with equation 3, a monofunctional β-keto ester, preferably a methyl or ethyl ester of the general formula V, is reacted with a polyhydric alcohol of the general formula IV to give the polyfunctional β-keto ester of the general formula II. The transesterification reaction for the preparation of monofunctional β-keto esters of the general formula II is known and is described by A. R. Bader et al. in J. Amer. Chem. Soc., 73, 4195 et seq. (1951).

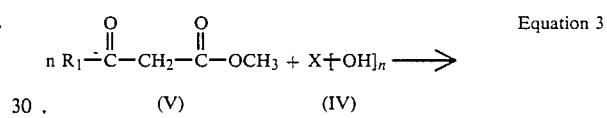

Equation 3

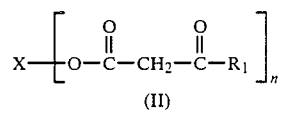

In the reaction sequence according to equation 2, the amount of the mono- or polyfunctional alcohol in question of the general formula IV required for the desired degree of conversion is added to the derivative in question of 5-acyl-Meldrum's acid of the general formula III and the mixture is then dissolved in about 5 to 20 times, preferably 10 times, the amount of a solvent which does not react with alcohols or Meldrum's acid, for example of a ketone, such as acetone or ethyl methyl ketone, or an ether, such as 1,2-dimethoxyethane or dioxane, if necessary with warming. The clear solution is heated to a temperature of about 60° C. to 120° C., preferably from 80° C. to 100° C. The start of the reaction manifests itself by vigorous evolution of carbon dioxide The mixture is stirred at the given temperature for about 1 to 6 hours, preferably 2 to 3 hours, until no further evolution of $CO_2$ can be observed.

The solvent is then removed in vacuo. Although the β-keto ester in question of the general formula II is obtained in a high purity, the product can be further purified, if appropriate, by methods known to one skilled in the art.

Particularly suitable derivatives of 5-acyl-Meldrum's acid of the general formula III are those in which $R^1$ denotes cyclobutyl, butyl, pentyl, cyclopentyl, hexyl, cyclohexyl, heptyl, octyl, nonyl or higher alkyl radicals having up to about 22 carbon atoms, which are optionally substituted by further alkyl radicals, alkoxyalkyl radicals, aryl radicals, alkoxyaryl radicals, aryloxyaryl radicals or halogen atoms or by other functional groups, for example by terminal acid ester functions, or in which individual $CH_2$ groups can be replaced by oxygen or sulfur atoms or by groups such as —C(O)—O—, —C(O)—NR$^2$—, NR$^2$—C(O)—NR$^3$—, —O—C(O)—NR$^2$—, —O—C(O)—O— or —NR$^2$—, in which R$^2$ and R$^3$ have the meaning described above.

Particularly preferred radicals R$^1$ which may be mentioned are t-butyl, n-hexyl, 2,5-dioxahexyl, cyclopentyl, cyclohexyl, benzyl, phenoxymethyl and nonyl. The t-butyl, cyclohexyl and phenoxymethyl radicals are particularly preferred.

Alcohols of the general formula IV which can be used are alcohols which are di- or trifunctional or of higher functionality; alcohols which contain 2 to 6 OH groups per molecule are preferred. Difunctional alcohols of the general formula IV include, for example, ethylene glycol, propane-1,2-diol, propane-1,3-diol, 2,2-dimethylpropane-1,3-diol, 3-chloropropane-1,2-diol, butane-1,2-diol butane-1,3-diol, butane-2,3-diol, butane-1,4-diol, 2,3dimethylbutane-2,3-diol, pentane-1,2-diol, pentane-1,5-diol, pentane-2,4-diol 2-methyl-pentane-2,4-diol, hexane-1,6-diol, hexane-2,5-diol, 2,5-dimethylhexane-2,5-diol, 2-ethylhexane-1,3-diol, octane-1,8-diol, decane-1,10-diol, dodecane-1 2-diol, dodecane-1,12-diol and phenylethylene glycol, or higher optionally substituted and branched alkanediols, such as tartaric acid, dimethyl tartrate, diethyl tartrate, diisopropyl tartrate, 3-allyloxy-1,2-propanediol, dihydroxyacetone or tetraphenyl-1,2-ethanediol, in which one or more methylene groups can optionally be replaced by radicals containing oxygen atoms, such as, for example, in diethylene glycol, triethylene glycol, tetraethylene glycol, dipropylene glycol or 2,3-benzylidenethreitol, by radicals containing sulfur atoms, such as in 2,2-thiodiethanol or 1,8-dihydroxy-3,6-dithiaoctane, or by radicals containing nitrogen atoms, such as, for example in N-methyl-2,2'-iminodiethanol, N-butyl-2,2'-iminodiethanol, N-tert-butyl-2,2'-iminodiethanol or N-phenyl-2,2'-iminodiethanol, or by the groups described above. Unsaturated diols, such as, for example, 2-butene-1,4-diol, 2-butyne-1,4-diol, 3-hexyne-2,5-diol or 2,5-dimethyl-3-hexyne-2,5-diol, or cyclic diols, which can in turn be substituted by oxygen, sulfur or nitrogen atoms such as cyclohexane-1,2-diol, cyclohexane-1,4-diol, 1,4-bis(hydroxymethyl)-cyclohexane or 1,4-bis(2-hydroxyethyl)-piperazine, can moreover also advantageously be employed. Such diols are in general commercially available. Other diols can be prepared, for example, by reaction of diols containing primary amino groups, for example 2-amino-2-methyl-1,3-propanediol, with monofunctional acid derivatives, such as carboxylic acid chlorides or sulfonic acid chlorides, or monofunctional isocyanates, and also with difunctional acid derivatives or corresponding isocyanates.

Trifunctional alcohols are preferably derived from glycerol, from higher α,β,ω-triols or from triethanolamine. It is also possible for higher-chain derivatives, in particular ethoxylated compounds and heterocyclic compounds, such as, for example, 1,3,5-tris(2-hydroxyethyl)-cyanuric acid, similarly to be used. Glycerol, 2-hydroxymethyl-2-methylpropane-1,3-diol, 2-ethyl-2-hydroxymethylpropane-1,3-diol, 2,3-isopropylidene-erythruronic acid, hexane-1,2,6-triol, 1,1,1-triethanolamine, 1,1,1-tripropanolamine and partly acetalized or ketalized sugar derivatives are mentioned.

Reaction products of tetrafunctional alcohols or aminotriols with acid derivatives, isocyanates or cyclic carbonates can moreover also be used. Alcohols of higher functionality of the general formula III are derived, for example, from condensation products of glycerol or pentaerythritol or from reaction products of difunctional acid derivatives or isocyanates with alcohols or aminoalcohols of higher functionality. The list of alcohols which can be used is thus by no means complete; practically all alcohols which contain no other group which reacts with acid esters or which react homogeneously under the reaction conditions described to form esters can be used.

In the preparation of β-keto esters of the general formula II by transesterification in accordance with equation 3, monofunctional β-keto esters of the general formula V are employed with alcohols of the general formula IV such that about a 5 to 200% excess, preferably a 10 to 50% excess, of a β-keto ester esterified with a low molecular weight alcohol, for example a methyl or ethyl ester, is reacted at about 100° to 160° C., preferably at 120° to 140° C. If appropriate, a solubilizing agent, such as dimethylformamide or N-methylpyrrolidone, can be added to increase the solubility of the alcohol of the general formula IV in the β-keto ester of the general formula V. By applying a weak vacuum of about 800 to 20 mm Hg, preferably 400 to 100 mm Hg, the equilibrium is shifted continuously in the desired direction by distilling off the lower alcohol formed. When the theoretical amount of lower alcohol has distilled off, the excess β-keto ester esterified with a low molecular weight alcohol of the general formula V and if appropriate the solubilizing agent added are distilled off under a high vacuum. The β-keto ester of the general formula II, which is often obtained as an oil, remains as the residue usually in a very high purity, so that it can be used for the diazo transfer without further purification.

The β-keto esters of the general formula V esterified with a low molecular weight alcohol required in this reaction sequence are in some cases commercially available or can be prepared by numerous methods which are known from the literature. Their preparation from the corresponding derivatives of 5-acyl-Meldrum's acid according to the general formula III is particularly preferred here. Although an additional reaction step is taken in this procedure in comparison with process variant improved yields and/or purer β-keto esters of the general formula II can be achieved with this variant.

The compounds according to the invention are used in radiation-sensitive mixtures, since they have high light sensitivity, in particular when exposed to light having a wavelength between about 190 to 300 nm. Since the mixtures fade very well when exposed, structurings can be produced which are distinctly superior to those of the known mixtures with respect to their resolution capacity The use of the radiation-sensitive compounds according to the invention is described in German patent application P 3,900,736.7, corresponding to U.S. application No. 07/466,007, filed at the same time.

The following examples for the preparation of the α-diazo-β-keto esters according to the invention of the general formula I describe the invention but are not intended to limit it.

EXAMPLE 1

Preparation of a difunctional α-diazo-β-keto ester of the general formula I: bis-2,9-diazo-1,10-dicyclohexyl-4,7-dioxa-1,3,8,10-tetraoxo-decane (3)

Stage 1:

5-(1-Cyclohexyl-1-hydroxymethyl)-2,2-dimethyl-1,3-dioxane-4,6-dione (1)

A solution consisting of 144 1 g (1.0 mol) of 2,2-dimethyl-1,3-dioxane-4,6-dione and 158.2 g (2.0 mol) of pyridine in 500 ml of methylene chloride is cooled to 10° C. 146.6 g (1.0 mol) of cyclohexanecarbonyl chloride are added dropwise at this temperature, while stirring. The reaction mixture is then warmed to room temperature, and after 4 hours a mixture of 500 g of ice, 500 ml of water and 100 ml of concentrated hydrochloric acid is added. The organic phase is washed twice with 400 ml of water, dried over magnesium sulfate and then freed from the solvent.

An oily red residue remains which is boiled up twice with 600 ml of n-hexane each time, with addition of active charcoal On cooling, fine, pale yellow-colored crystals of the desired compound (1) precipitate out of the n-hexane solution. After further recrystallization from n-hexane, white crystals of the compound (1) of melting point 82° C. are obtained in a yield of 57%.

Stage 2:
1,10-Dicyclohexyl-4,7-dioxa-1,3,8,10-tetraoxo-decane (2)

12.4 g (0.2 mol) of ethylene glycol and 101.8 g (0.4 mol) of the compound (1) described above are introduced into 800 ml of ethyl methyl ketone and the mixture is heated slowly. From about 60° C., vigorous evolution of carbon dioxide starts. The solution is kept under reflux for 2.5 hours. After the reaction mixture has cooled, the solvent is stripped off in vacuo. An oily residue which consists virtually exclusively of the desired difunctional β-keto ester (2) remains. It is used as the starting product for the next stage without further purification.

Stage 3:
Bis-2,9-diazo-1,10-dicyclohexyl-4,7-dioxa-1,3,8,10-tetraoxo-decane (3)

11.5 g (30 mmol) of the β-keto ester (2) are dissolved in 130 ml of acetonitrile and the solution is cooled to 0° C. 9.85 g (50 mmol) of tosyl azide are added to the cooled solution, while stirring, and 6.6 g (65 mmol) of triethylamine are then added dropwise so that the temperature does not rise above 5° C. The mixture is stirred at this temperature for 10 minutes; it is then warmed to room temperature. After two hours, no further tosyl azide is detectable in the reaction mixture by thin layer chromatography (silica gel, mobile phase: $CH_2Cl_2$) 3.4 g (15 mmol) of 4-carboxyphenylsulfonyl azide are added to the mixture, while cooling. After further reaction at room temperature for a further 2 hours, a precipitate forms. The mixture is concentrated on a rotary evaporator, the residue is taken up in diethyl ether, the mixture is extracted twice with in each case 5% strength aqueous potassium hydroxide solution and the extract is washed neutral with water. The organic phase is separated off and dried over magnesium sulfate. After concentration thereof, 12.2 g of a pale yellowish oil, which is freed from solvent residues by application of a high vacuum, remain. Chromatography on silica gel using methylene chloride as the mobile phase yields the colorless product (3), which has the following composition.

$C_{22}H_{18}N_4O_6$ (molecular weight 434.41): calculated: C 60.8%, H 4.2%, N 12.9%, found: C 60.7%, H 4.3%, N 13.0%.

IR (film) 2,140.7 $cm^{-1}$ (C=$N_2$).

EXAMPLE 2

Preparation of an unsaturated difunctional α-diazo-62-keto ester of the general formula I bis-4,13-diazo-6,11-dioxa-2,2,15,15-tetramethyl-3,5,12,14-tetraoxo-hexadec-8-yne (5)

Stage 1:
6,11-Dioxa-2,2-15,15-tetramethyl-3,5,12,14-tetraoxo-hexadec-8-yne (4)

8.6 g (0.1 mol) of 2-butyne-1,4-diol are heated to 120° C. together with 47.5 g (0.3 mol) of methyl 4,4-dimethyl-3-oxovalerate, while stirring. The methyl alcohol formed during this procedure is distilled off into a cooled receiver. After about 4 hours, the theoretically calculated amount of methyl alcohol is distilled off. The homogeneous solution is heated at 140° C. for 1 hour and excess 4,4-dimethyl-3-oxovaleric acid is distilled off by applying a vacuum (10 mm Hg). The residue which remains virtually corresponds to the pure compound (4) and is further processed without additional purification.

Stage 2:
Bis-4,13-diazo-6,11-dioxa-2,2,15,15-tetramethyl-3,5,12,14-tetraoxo-hexadec-8-yne (5)

30.4 g (90 mmol) of the product (4) described above are dissolved in 250 ml of acetonitrile and the solution is cooled to 0 C. 33.6 g (170 mmol) of tosyl azide are added dropwise in portions, while stirring, so that the temperature does not exceed 5° C. The mixture is warmed to room temperature. After about 2 hours, no further tosyl azide can be detected by thin layer chromatography. 4.5 g (20 mmol) of 4-carboxybenzenesulfonyl azide are added to the mixture. After two hours, the solvent is distilled off on a rotary evaporator, the solid residue is taken up in methylene chloride and the mixture is washed with 2×200 ml of 4% strength potassium hydroxide solution and then with 200 ml of water. After drying and removal of the solvent, an oil remains, which starts to crystallize in the refrigerator. The crystal cake (29.8 g=85% of theory) is recrystallized from n-hexane 22.2 g of colorless crystals of the compound (5) of melting point 69°–70° C. are obtained.

$C_{18}H_{22}N_4O_6$ (molecular weight 390.40): calculated: C 55.38, H 5.68, N 14.35, found: C 55.4, H 5.6, N 14.4.

IR (KBR): 2,137.9 $cm^{-1}$, 2,160.0 $cm^{-1}$ (shoulder) (C=$N_2$).

EXAMPLE 3

Preparation of a trifunctional α-diazo-β-keto ester of the general formula I tris-[(5-diazo-3,8-dioxa-4,6-dioxo-8-phenyl)-octyl]-amine (8)

Stage 1:
5-(1-Hydroxy-2-phenoxyethylidene)-2,2-dimethyl-1,3-dioxane-4,6-dione (6)

93.8 g (0.55 mol) of phenoxyacetyl chloride are added dropwise to a solution, cooled to 8° C., of 72.1 g (0.5 mol) of 2,2-dimethyl-1,3-dioxane-4,6-dione and 79.1 g (1.0 mol) of pyridine in 250 ml of methylene chloride so that the temperature does not rise above 10° C. The mixture is subsequently stirred at room temperature for 2.5 hours, a mixture of 250 g of ice, 250 ml of water and 30 ml of concentrated hydrochloric acid is added and the mixture is extracted by shaking. The organic phase is washed twice with 100 ml of water each time and dried over magnesium sulfate. The solvent is distilled off, a solid remaining, which is recrystallized from t-butyl methyl ether. 72 g (52% of theory) of white crystals of the compound (6), which melt at 85°–87° C., with decomposition, are obtained.

Stage 2:
Tris-[(3,8-dioxa-4,6-dioxo-8-phenyl)-octyl]amine (7)

3.6 g (20 mmol) of triethanolamine and 18 g (64 mmol) of the compound (6) described above are heated under reflux in 140 ml of methyl ethyl ketone. When the evolution of carbon dioxide has ended, the mixture is heated under reflux for a further hour and the solvent is then distilled off. A highly viscous reddish oil of the compound (7) remains, which is employed for the subsequent reaction stage without further purification.

Stage 3:
Tris-[(5-diazo-3,8-dioxa-4,6-dioxo-8-phenyl)octyl]-amine (8)

The total amount of the oil (7) formed in stage 2 (about 20 mmol) is dissolved in 120 mol of acetonitrile and the solution is cooled to 0° C. 6.5 g (65 mmol) of triethylamine are added to the cooled solution, while stirring, and 12.8 g (65 mmol) of tosyl azide are then added dropwise in a manner such that the temperature does not rise above 5° C. The mixture is stirred at this temperature for 10 minutes and then warmed to room temperature. After three hours, the clear solution is evaporated to dryness on a rotary evaporator, the residue is taken up in diethyl ether, the mixture is extracted twice with 100 ml of 5% strength aqueous potassium hydroxide solution each time and the extract is then washed neutral with water. The organic phase is separated off and dried over magnesium sulfate. After concentration on a rotary evaporator, 15.4 g of a pale brownish oil remain, which is freed from solvent residues by applying a high vacuum. During this procedure, crystals start to separate out. The crystal slurry is recrystallized from toluene to form 12.1 g of colorless crystals of the compound (8), which melt at 104° C. with the start of decomposition.

$C_{36}H_{33}N_7O_{12}$ (molecular weight 707.70) calculated: C 61.10%, H 4.70%, N 13.85%, found: C 61.0%, H 4.7%, N 14.1%.

IR (KBr): 2,142 cm$^{-1}$ (C=N$_2$).

EXAMPLE 4

Preparation of a trifunctional α-diazo-β-keto ester of the general formula I:
tris-[(5-diazo-7,7-dimethyl-4,6-dioxo-3-oxa)-octyl]-amine (10)

Stage 1:
Tris-[(7,7-dimethyl-4,6-dioxo-3-oxa)-octyl]amine (9)

7.5 g (50 mmol) of triethanolamine and 30 g (189 mmol) of methyl 4,4-dimethyl-3-oxovalerate are heated at 130° C. for 5 hours, while stirring. The methyl alcohol formed during this procedure is distilled off. The excess monofunctional β-keto ester is then distilled off in vacuo. A pale yellow oil remains, which proves to be an almost pure compound (9), so that it can be used for the subsequent reaction stage without further purification.

Stage 2:
Tris-[(5-diazo-7,7-dimethyl-4,6-dioxo-3-oxa)-octyl]-amine (10)

18 g (34 mmol) of the compound (9) from stage 1 are dissolved in 180 ml of acetonitrile and the solution is cooled to 0° C. 11.4 g (112 mmol) of triethylamine are added to the cooled solution, while stirring, and 22.4 g (112 mmol) of tosyl azide are then added dropwise so that the temperature does not rise above 5° C. The mixture is stirred at this temperature for 10 minutes and then warmed to room temperature. After two hours, the clear solution is concentrated to dryness on a rotary evaporator, the residue is taken up in diethyl ether, the mixture is extracted twice with 100 ml of 5% strength aqueous potassium hydroxide solution each time and the extract is washed neutral with water. The organic phase is separated off and dried over magnesium sulfate. After concentration on a rotary evaporator, 18.4 g of a pale brownish oil remain, which is freed from solvent residues by applying a high vacuum. During this procedure, crystals start to separate out. The crystal slurry is recrystallized from cyclohexane to give 15.4 g of colorless crystals of the compound (10), which melt at 101° C., with slow decomposition.

$C_{27}H_{39}N_7O_9$ (molecular weight 605.65): calculated: C 53.55%, H 6.49%, N 1619%, found: C 53.5%, H 6.7%, N 16.1%.

IR (KBr): 2,171 cm$^{-1}$, 2,134 cm$^{-1}$ (shoulder) (C=N$_2$).

EXAMPLE 5

Preparation of a trifunctional α-diazo-β-keto ester of the general formula I:
N-phenyl-N'-[1,1-bis-(5-cyclohexyl-4-diazo-3,5-dioxo-2-oxa-pentyl)-6-cyclohexyl-5-diazo-4,6-dioxo-3-oxa-hexyl]urea (13)

Stage 1:
N-Phenyl-N'-[1,1-bis-hydroxymethyl-2-hydroxyethyl]urea (11)

66.6 g (0.55 mol) of tris(hydroxymethyl)aminomethane are dissolved in 200 ml of distilled water, and 400 ml of acetone are added. 59.6 g (0.5 mol) of phenyl isocyanate are added dropwise, while stirring, whereupon a heavy white precipitate forms. When the addition has ended, the mixture is stirred for a further 2 hours and the precipitate is filtered off with suction. It is then digested successively with in each case 150 ml of water, acetone and diethyl ether. Finally, the compound (11), which is obtained in virtually analytically pure form, is dried at 75.C.

Stage 2:
N-Phenyl-N'-[1,1-bis-(5-cyclohexyl-3,5-dioxo-2-oxapentyl)-6-cyclohexyl-4,6-dioxo-3-oxahexyl]-urea (12)

8.4 g (35 mmol) of the compound (11) and 22.0 g (119 mmol) of methyl 3-cyclohexyl-3-oxo-propionate are heated at 130° C. in a Claisen apparatus for 4 hours under application of a weak vacuum, the methyl alcohol formed being distilled off. The excess methyl 3-cyclohexyl-3-oxo-propionate (boiling point 75°–76° C./0.05 mm Hg) is then distilled off from the mixture. A brownish highly viscous oil of N-phenyl-N'-[1,1-bis-(5-cyclohexyl-3,5-dioxo-2-oxa-pentyl)-6-cyclohexyl-4,6-dioxo-3-oxa-hexyl]-urea (12) remains and can be further used without additional purification.

Stage 3:
N-Phenyl-N,-[1,1-bis-(5-cyclohexyl-4-diazo-3,5-dioxo-2-oxa pentyl)-6-cyclohexyl-5-diazo-4,6-dioxo-3-oxa-hexyl]-urea (13)

13.72 g (20 mmol) of the compound (12) described above and 6.6 g (65 mmol) of triethylamine are dissolved in 140 ml of acetonitrile and the solution is cooled to 0° C. 12.8 g (65 mmol) of toluenesulfonyl azide are added dropwise to this solution so that the temperature does not rise above 5° C. The mixture is warmed to room temperature and subsequently stirred for 4 hours. The clear solution is then evaporated to dryness on a rotary evaporator, the residue is taken up in methylene chloride, the mixture is extracted twice with 100 ml of 5% strength aqueous potassium hydroxide solution each time and the extract is washed neutral with water. The organic phase is separated off and dried over magnesium sulfate. After concentration on a rotary evaporator, 12.4 g of a pale brownish oil remain, which is freed from solvent residues by applying a high vacuum. The oil is taken up again in a small amount of methylene chloride and eluted over a silica gel column. By using methylene chloride/ethyl acetate 5:1 as the mobile phase and after concentration of the solvent, 8.5 g (55.6% of theory) of a pale yellowish oil of the compound (13) is obtained.

$C_{38}H_{48}N_8O_{10}$ (molecular weight 764.76): calculated: C 58.91%, H 5.98%, N 14.46%, found: C 59.2%, H 6.0%, N 14.5% .

IR (KBr): 2,141.2 cm$^{-1}$ (C=N$_2$).

EXAMPLE 6

Preparation of a trifunctional α-diazo-β-keto ester of the general formula I: 2,2,2-tris[4-(7-cyclohexyl-6-diazo-1,4-dioxa-5,7-dioxoheptyl)-phenyl]-ethane (15)

Stage 1:
2,2,2-Tris-[4-(7-cyclohexyl-1,4-dioxa-5,7-dioxo-heptyl)-phenyl]-ethane (14)

8.77 g (20 mmol) of 2,2,2-tris-[4-(2-hydroxyethoxy)-phenyl]-ethane (prepared by reaction of tris-(4-hydroxyphenyl)-ethane with 2-chloroethanol) are heated at 130° C. with 18.4 g (100 mmol) of methyl 3-cyclohexyl-3-oxo-propionate in a Claisen apparatus for 4 hours with application of a weak vacuum. The methyl alcohol formed is distilled off, as is the excess methyl 3-cyclohexyl-3-oxo-propionate (boiling point 75 76° C./0.05 mm Hg). A pale brownish-colored highly viscous oil of the compound (14) remains and is further used without additional purification.

Stage 2:
2,2,2-Tris-[4-(7-cyclohexyl-6-diazo-1,4-dioxa-5,7-dioxoheptyl)-phenyl]-ethane (15)

8.95 g (10 mmol) of the compound (14) described above and 3.5 g (35 mmol) of triethylamine are dissolved in 100 ml of acetonitrile and the solution is cooled to 0° C. 6.9 g (35 mmol) of toluenesulfonyl azide are added dropwise to this solution so that the temperature does not rise above 5° C. The mixture is warmed to room temperature and subsequently stirred for 4 hours. The clear solution is then evaporated to dryness on a rotary evaporator, the residue is taken up in methylene chloride, the mixture is extracted twice with 100 ml of 5% strength aqueous potassium hydroxide solution each time and the extract is washed neutral with water. The organic phase is separated off and dried over magnesium sulfate. After concentration on a rotary evaporator, 9.4 g of a pale brownish oil remain, which is freed from solvent residues by applying a high vacuum. The oil starts to crystallize immediately. The crystal slurry is recrystallized from t-butyl methyl ether. The compound (15) is obtained in the form of a white powder in virtually quantitative yield and has a melting point of 96° C.

$C_{53}H_{60}N_6O_{12}$ (molecular weight 973.09): calculated: C 65.42%, H 6.22%, N 8.64%, found: C 65.4%, H 6.3%, N 8.4%.

IP: (KBr): 2,141.2 cm$^{-1}$ (C=N$_2$).

EXAMPLE 7

Preparation of a tetrafunctional α-diazo-β-keto ester of the general formula I:
N-[1,1-bis-(5-cyclohexyl-4-diazo-3,5-dioxo-2-oxa-pentyl)-6-cyclohexyl-5- diazo-4,6-dioxo-3-oxa-hexyl]-O-(6-cyclohexyl-5-diazo-4,6-dioxo-3-oxa-hexyl)-urethane (18)

Stage 1:
N-(Bis-1,1-hydroxymethyl-2-hydroxyethyl)-O-(2-hydroxyethyl)-urethane (16)

88.6 g (1 mol) of ethylene carbonate and 121.2 g of tris-(hydroxymethyl)-aminomethane are mixed with one another. The mixture heats up and is kept at not more than 70° C. by external cooling. When the exothermic reaction has ended, the mixture is stirred at this temperature for a further 6 hours. On cooling, a melt forms, which is recrystallized from acetone. 198 g of white crystals of melting point 112° C. are obtained.

Stage 2:
N-[1,1-Bis-(5-cyclohexyl-3,5-dioxo-2-oxapentyl)-6-cyclohexyl-4,6-dioxo-3-oxa-hexyl]-O-(6-cyclohexyl-4,6-dioxo-3-oxa-hexyl)-urethane (17)

6.27 g (30 mmol) of the compound (16) from stage 1 are heated at 140° C. with 25.0 g (136 mmol) of methyl cyclohexylacetoacetate. The theoretical amount of methyl alcohol is distilled off from the mixture in the course of 4 hours. The excess methyl cyclohexylacetoacetate is then distilled off in vacuo and the pale brownish residue of the compound (17) is further processed without additional purification.

Stage 3:
N-[1,1-Bis-(5-cyclohexyl-4-diazo-3,5-dioxo-2-oxa-pentyl)-6-cyclohexyl-5-diazo-4,6-dioxo-3-oxahexyl]-O-(6-cyclohexyl-5-diazo-4,6-dioxo-3-oxahexyl)-urethane (18)

24.5 g (30 mmol) of the compound (17) are dissolved in 250 ml of acetonitrile and the solution is cooled to 0° C. 13.4 g (130 mmol) of triethylamine are added to the cooled solution, while stirring. 25.6 g (130 mmol) of tosyl azide are then added dropwise so that the temperature does not rise above 5° C. The mixture is stirred at this temperature for 10 minutes and then warmed to room temperature. After 3 hours, the clear reddish-brown solution is concentrated to dryness on a rotary evaporator, the residue is taken up in methylene chloride, the mixture is extracted twice with 100 ml of 5% strength aqueous potassium hydroxide solution each time and the extract is washed neutral with 5% strength aqueous sodium chloride solution. The organic phase is then separated off and dried over magnesium sulfate. After concentration of the solution on a rotary evaporator, 26.7 g of a brownish oil remain, which is freed from solvent residues by application of a high vacuum. By addition of diethyl ether, small amounts of pale yellowish crystals start to separate out. These are separated off and prove to be N-[1,1-bis-(5-cyclohexyl-4-diazo-3,5-dioxo-2-oxapentyl) 6-cyclohexyl-5-diazo 4,6-dioxo-3-oxa-hexyl]-O-(6-cyclohexyl-5-diazo-4,6-dioxo-3-oxahexyl) urethane (18). The solution which remains is chromatographed on silica gel using methylene chloride in order to isolate residual traces of the compound (18). Excess tosyl azide is eluted during this procedure. The main fraction is eluted with a mixture of methylene chloride/ethyl acetate (75% of the amount employed), crystallization of the compound (18) starting after the solvent has been distilled off.

$C_{43}H_{55}N_9O_{14}$ (molecular weight 921.96): calculated: C 56.02%, H 6.01%, N 13.62%, found: C 56.1%, H 5.8%, N 13.4%.

IR (KBr): 2,140.6 cm$^{-1}$ (C=N$_2$).

EXAMPLE 8

Preparation of tetrafunctional α-diazo-β-keto ester of the general formula I:
N,N,N',N'-tetrakis-[6-cyclohexyl-5-diazo-4,6-dioxo-3-oxahexyl]-ethylenediamine (20)

Stage 1:
N,N,N',N'-Tetrakis-6-cyclohexyl-4,6-dioxo-3-oxa-hexylethylenediamine (19)

5.9 g (25 mmol) of N,N,N',N'-tetrakis-(2-hydroxyethyl)-ethylenediamine are heated at 130° C. with 33.1 g (180 mmol) of methyl 3-cyclohexyl-3-oxo-propionate for 7.5 hours, during which the methyl alcohol formed is distilled off. The excess methyl 3-cyclohexyl-3-oxo-propionate is then distilled off in vacuo. An orange-yellow viscous oil of the very pure compound (19) is obtained in quantitative yield. This is employed in the next reaction stage without further purification.

Stage 2:
N,N,N',N'-Tetrakis-[6-cyclohexyl-5-diazo-4,6-dioxo-3-oxa-hexyl]-ethylenediamine (20)

19.8 g (23 mmol) of the compound described above are dissolved in 200 ml of acetonitrile. 20.6 g (104 mmol) of tosyl azide are added to the solution, which has been cooled to 0° C., and 10.8 g (107 mmol) of triethylamine are then added dropwise so that the temperature does not rise above 50° C. After three hours, the clear reddish solution is evaporated to dryness on a rotary evaporator, the residue is taken up in an ether/methylene chloride (3:1) mixture, the mixture is extracted twice with 100 ml of 5% strength aqueous potassium hydroxide solution each time and the extract is washed neutral with 5% strength aqueous sodium chloride solution. The organic phase is separated off and dried over magnesium sulfate. On concentration on a rotary evaporator, the almost pure product (20) is already obtained as crystals in a yield of 95%. An analytically pure sample is prepared by recrystallization from ethanol, yielding white crystals of melting point 112°-114° C.

$C_{46}G_{64}N_{10}O_{12}$ (molecular weight 949.07): calculated: C 58.22%, H 6.80%, N 14.76%, found: C 58.1%, H 7.0% N 14.5%.

IR (KBr): 2,140.6 cm$^{-1}$ (C=N$_2$)

EXAMPLE 9

Preparation of a hexafunctional α-diazo-β-keto ester of the general formula I:
1,19-biscyclohexyl-2,18-bis-diazo-6,14-[bis-(4-cyclohexyl-3-diazo-2,4-dioxo-1-oxa)-butyl]-10-[8-(cyclohexyl-7-diazo-1,5-dioxa-6,8-dioxo-3-(3-cyclohexyl-3-diazo-2,4-dioxo-oxa-butyl))-1,5-dioxa-6,8-dioxooctyl]-4,8,12,16-tetraoxa-1,3,17,19-tetraoxononadecane (22)

Stage 1:
1,19-Bis-cyclohexyl-6,14-[bis-(4-cyclohexyl-2,4-dioxo-1-oxa)-butyl]-10-[8-(cyclohexyl-1,5-dioxa-6,8-dioxo-3-(3-cyclohexyl-2,4-dioxo-1-oxabutyl))-1,5-dioxa-6,8-dioxo-octyl]-4,8,12,16-tetraoxa-1,3,17,19-tetraoxo-nonadecane (21)

6.32 g (20 mmol) of tetraglycerol are heated at 130° C. with 33.1 g (180 mmol) of methyl 3-cyclohexyl-3-oxo-propionate for 7.5 hours, the methyl alcohol formed being distilled off. The excess methyl 3-cyclohexyl-3-oxo-propionate is then distilled off in vacuo. A virtually colorless vitreous product of very pure 1,19-bis-cyclohexyl-6,14-bis-[4-cyclohexyl-2,4-dioxo-1-oxa-butyl]-10-[8-cyclohexyl-1,5-dioxa-6,8-dioxo-3-(3-cyclohexyl-2,4dioxo-1-oxa-butyl)octyl]-4,8,12,16-tetraoxa-1,3,17,19-tetraoxo-nonadecane (21) is obtained in a quantitative yield. This is employed in the next reaction stage without further purification.

Stage 2:
1,19-Bis-cyclohexyl-2,18-bis-diazo-6,14-b is[3-diazo-4-cyclohexyl-2,4-dioxo-1-oxa-butyl]-10-[8-cyclohexyl-7-diazo-1,5-dioxa-6,8-dioxo-3-(3-cyclohexyl-3-diazo-2,4-dioxo-1-oxa-butyl)octyl]-4,8,12,16-tetraoxa-1,3,17,19-tetraoxo-nonadecane (22)

12.3 g (10 mmol) of the compound (21) are dissolved in 150 ml of acetonitrile, and 11.8 g (60 mmol) of tosyl azide and 6.1 g (60 mmol) of triethylamine are added, as described above. After warming to room temperature, the mixture is stirred for 8 hours and worked up as described above. Half of the product mixture is eluted over a silica gel column, a pale yellow fraction being isolated by using the mobile phase methylene chloride/ethyl acetate (6:1). After concentration, a yellowish oil remains.

$C_{66}H_{86}N_{12}O_{21}$ (molecular weight 1383.48): calculated: C 57.30%, H 6.27%, N 12.15%, found: C 56.7%, H 6.5%, N 11.9%.

IR (film): 2,138.4 cm$^{-1}$ (C=N$_2$).

EXAMPLE 10

As described in Example 7, 10 g (73.5 mmol) of pentaerythritol are reacted with 55.2 g of methyl 3-cyclohexyl-3-oxo-propionate and the mixture is worked up. A tetrafunctional ester (compound 23) in which $R^1$ denotes $C_6H_{11}$ can be isolated. It is obtained as a viscous oil in virtually quantitative yield.

The ester (23) is then reacted with 59.1 g (300 mmol) of toluenesulfonyl azide and 30.6 g (300 mmol) of triethylamine in 200.0 g of acetonitrile to give the corresponding tetrafunctional α-diazo-β-keto ester of the general formula I. The compound (25) is purified by recrystallization from ethanol. It has a melting point of 123°-125° C.

$C_{41}H_{52}N_8O_{12}$ (molecular weight 848.91): calculated: C 58.01%, H 6.17%, N 13.20%, found: C 58.2%, H 6.2%, N 13.2%.

EXAMPLE 11

(Comparison Example)

As in Example 10, 10 g of pentaerythritol are converted into a tetrafunctional ester (compound 24), but in this case using 39.0 g of methyl acetoacetate, so that $R^1$ denotes $CH_3$.

The compound (24) is then converted, as described in Example 10, into the corresponding tetrafunctional α-diazo-β-keto ester (26) of the general formula I and the compound (26) is recrystallized from ethanol. It has a melting point of 108°-120° C.

$C_{21}H_{20}N_8O_{12}$ (molecular weight 576.43): calculated: C 43.76%, H 3.50%, N 19.44%, found: C 43.9%, H 3.6%, N 19.5%.

As demonstrated in German patent application P 3,900,736 7, corresponding to U.S. application No. 07/466,007, filed at the same time, it is true that photosensitive mixtures which contain the compound according to Example 11 as the photoactive component show comparable bleaching properties in comparison with the compound of the general formula I according to the invention, but the image differentiating properties are not satisfactory.

EXAMPLES 12 TO 67

Further compounds of the general formula I are listed, which have been prepared analogously to the examples described so far. Because of the large number of compounds, these are characterized in the following tables in respect of the possible variations described in the general formula I. Quantitative determination of the nitrogen is sufficiently conclusive as an analytical value.

| No. | $R^1$ | m | X | n | calc./found N % |
|---|---|---|---|---|---|
| 12 | $C_6H_5—CH_2—$ | 2 | $—C_2H_4—$ | 0 | 12.90/13.0 |
| 13 | $CH_3O—C(O)—C_2H_4—$ | 2 | " | 0 | 12.22/12.5 |
| 14 | $CH_3—C(O)—C_2H_4—$ | 2 | " | 0 | 19.80/20.1 |
| 15 | $C_6H_5—CH_2—O—CH_2—$ | 2 | " | 0 | 11.24/11.2 |
| 16 | $n-C_4H_9—$ | 2 | $—CH_2CH_2CH_2—$ | 0 | 14.73/14.8 |
| 17 | 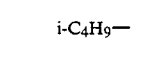 | 2 | $—CH_2—\overset{\mid}{CH}—CH_3$ | 0 | 14.33/14.2 |
| 18 | $i-C_4H_9—$ | 2 | $—CH_2—\overset{\mid}{CH}—CH_2CH_3$ | 0 | 14.20/14.3 |
| 19 | $n-C_{14}H_{29}—$ | 2 | $CH_3—\overset{\mid}{CH}—\overset{\mid}{CH}—CH_3$ | 0 | 8.30/8.3 |
| 20 | $n-C_6H_{13}—$ | 2 | $—C_2H_4—O—C_2H_4—$ | 0 | 12.44/12.6 |
| 21 | $t-C_4H_9—$ | 2 | $—C_2H_4—S—C_2H_4—$ | 0 | 13.14/13.1 |
| 22 | $C_6H_{11}—$ | 2 | $CH_3—N(C_2H_4)_2—$ | 0 | 15.51/15.3 |
| 23 | $C_6H_5—O—CH_2—$ | 2 | $—CH_2—(CH_2)_4—CH_2—$ | 0 | 10.72/10.8 |
| 24 | $n-C_4H_9—$ | 2 | $—CH_2—CH=CH—CH_2—$ | 0 | 14.28/14.1 |
| 25 | $C_6H_{11}—$ | 2 | $—CH_2—C≡C—CH_2—$ | 0 | 12.66/12.6 |
| 26 | $C_6H_5—CH_2—$ | 2 | " | 0 | 12.22/12.5 |
| 27 | $n-C_8H_{17}—$ | 2 | " | 0 | 11.15/11.2 |
| 28 | $CH_3OC(O)—C_2H_4—$ | 2 | " | 0 | 11.22/11.2 |
| 29 | $C_6H_{11}—$ | 2 | $—C_2H_4—O—\overset{O}{\overset{\|}{C}}—NH—C_2H_4—NH—\overset{O}{\overset{\|}{C}}—O—C_2H_4—$ | 0 | 14.18/13.9 |
| 30 | $CH_3OC_2H_4OCH_2—$ | 2 | 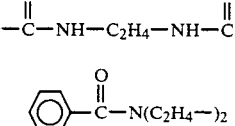 | 0 | 12.84/12.5 |
| 31 |  | 2 | 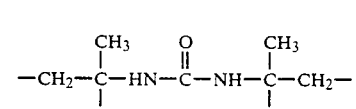 | 0 | 13.89/14.1 |
| 32 | $C_6H_{11}—$ | 2 | 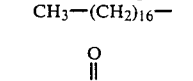 | 0 | 15.84/16.0 |
| 33 | $C_6H_5—CH_2—$ | 2 | " | 0 | 15.38/15.8 |
| 34 | $C_6H_{11}—$ | 2 | $—CH_2—\underset{CH_3}{\overset{CH_3}{\overset{\|}{\underset{\|}{C}}}}—HN—\overset{O}{\overset{\|}{C}}—NH—\underset{CH_3}{\overset{CH_3}{\overset{\|}{\underset{\|}{C}}}}—CH_2—$ | 0 | 15.94/16.2 |
| 35 | $t-C_4H_9—$ | 3 | $—CH_2—\overset{\mid}{CH}—CH_2—$ | 0 | 15.32/15.3 |
| 36 | $C_6H_{11}—$ | 3 | " | 0 | 13.41/13.2 |
| 37 | " | 3 | " | 1 | 12.49/12.2 |
| 38 | " | 3 | $N(C_2H_4—)_3$ | 0 | 14.34/14.5 |
| 39 | $CH_3—(CH_2)_7—$ | 3 | " | 0 | 12.67/12.4 |
| 40 | $C_6H_5—CH_2—$ | 3 | " | 0 | 13.85/13.9 |
| 41 | $CH_3—(CH_2)_{16}—$ | 3 | " | 0 | 8.51/8.2 |
| 42 | $H_5C_2O—\overset{O}{\overset{\|}{C}}—(CH_2)_3—$ | 3 | " | 0 | 12.57/12.3 |

-continued

| No. | R¹ | m | X | n | calc./found N % |
|---|---|---|---|---|---|
| 43 | t-C₄H₉— | 3 | C₆H₁₁—NH—C(O)—NH—C(CH₂—)₃ | 0 | 15.94/16.1 |
| 44 | i-C₄H₉— | 3 | " | 0 | 15.94/16.0 |
| 45 | C₆H₁₁— | 3 | " | 0 | 14.35/14.5 |
| 46 | t-C₄H₉— | 3 | C₆H₅—NH—C(O)—NH—C(CH₂—)₃ | 0 | 16.08/15.8 |
| 47 | C₆H₅—CH₂— | 3 | " | 0 | 14.03/14.6 |
| 48 | n-C₁₀H₂₁— | 3 | " | 0 | 11.81/12.0 |
| 49 | C₆H₁₁— | 3 | triazine-trione with three —C₂H₄— | 0 | 15.84/15.7 |
| 50 | C₆H₅—CH₂— | 3 | " | 0 | 15.30/15.6 |
| 51 | t-C₄H₉— | 3 | (—C₂H₄—O—C₆H₄—)₃C—CH₃ | 0 | 9.39/9.1 |
| 52 | C₆H₅—O—CH₂— | 3 | " | 0 | 8.04/8.5 |
| 53 | t-C₄H₉— | 4 | C(CH₂—)₄ | 0 | 15.05/14.9 |
| 54 | C₆H₅—CH₂— | 4 | " | 0 | 12.72/13.0 |
| 55 | C₆H₁₁— | 4 | H₅C₂—C(CH₂—)(CH₂—)—HN—C(O)—NH—C₆H₄—NH—C(O)—NH—C(CH₂—)(CH₂—)—C₂H₅ | 0 | 15.11/15.0 |
| 56 | C₆H₅—CH₂— | 4 | " | 0 | 14.70/15.1 |
| 57 | t-C₄H₉— | 4 | H₅C₂—C(CH₂—)(CH₂—)—HN—C(O)—NH—C₆H₁₀—NH—C(O)—NH—C(CH₂—)(CH₂—)—C₂H₅ | 0 | 16.43/16.8 |
| 58 | C₆H₁₁— | 4 | " | 0 | 15.04/15.2 |
| 59 | C₆H₁₁— | 4 | —C₂H₄—O—C(O)—NH—C(CH₂—)(CH₂—)(CH₂—) | 0 | 13.98/14.2 |
| 60 | t-C₄H₉— | 4 | (—C₂H₄—)₂N—C₂H₄—N(—C₂H₄—)₂ | 0 | 16.58/16.5 |
| 61 | n-C₆H₁₃— | 4 | " | 0 | 14.63/15.0 |
| 62 | t-C₄H₉— | 5 | cyclohexane with —H₂C, —H₂C, CH₂—, CH₂—, H | 0 | 14.28/14.5 |
| 63 | t-C₄H₉— | 5 | " | 1 | 13.52/12.8 |
| 64 | t-C₄H₉— | 6 | —H₂C—C(CH₂—)(CH₂—)—CH₂—O—CH₂—C(CH₂—)(CH₂—)—CH₂— | 0 | 14.40/14.7 |
| 65 | C₆H₁₁— | 6 | " | 0 | 12.70/12.4 |

-continued
| No. | R¹ | m | X | n | calc./found N % |
|---|---|---|---|---|---|
| 66 | i-$C_4H_9$— | 6 | —$CH_2$—CH—$CH_2$(—$OCH_2$—CH—$CH_2$—)$_2$$OCH_2$—CH—$CH_2$— | 0 | 13.70/13.2 |
| 67 | $C_4H_7$— | 6 | " | 0 | 13.52/13.2 |
| 68 | t-$C_4H_9$— | 8 | 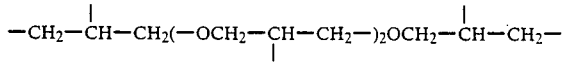 | 0 | 14.10/13.8 |
| 69 | $C_6H_{11}$— | 8 | " | 0 | 12.46/12.1 |
$C_4H_7$— = cyclobutyl-; $C_6H_{11}$— = cyclohexyl-.
Below the products from Examples 1 to 11, namely the compounds 3, 5, 8, 10, 13, 15, 18, 20, 22, 25 and 26 are shown by way of their formula.
Compound (3)
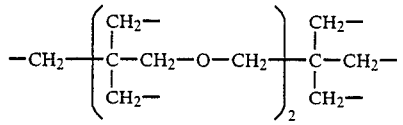
Compound (5)
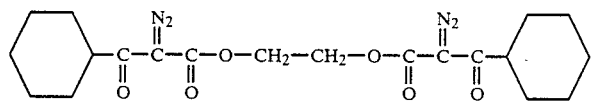
Compound (8)
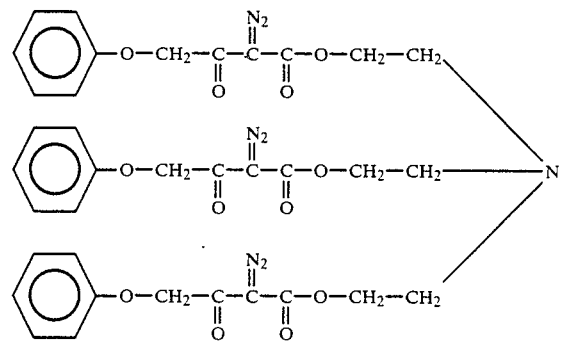
Compound (10)
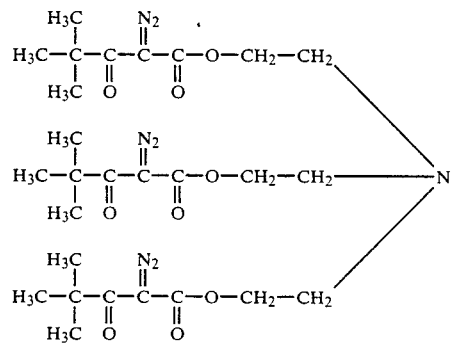

-continued
Compound (13)
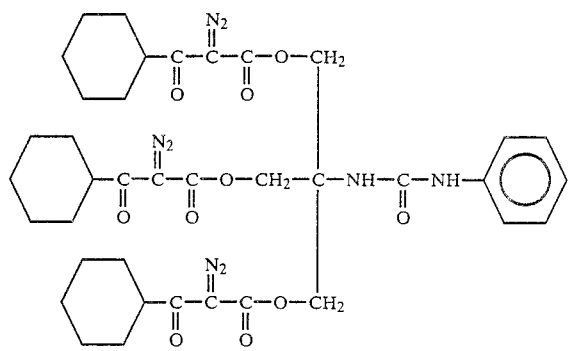
Compound (15)
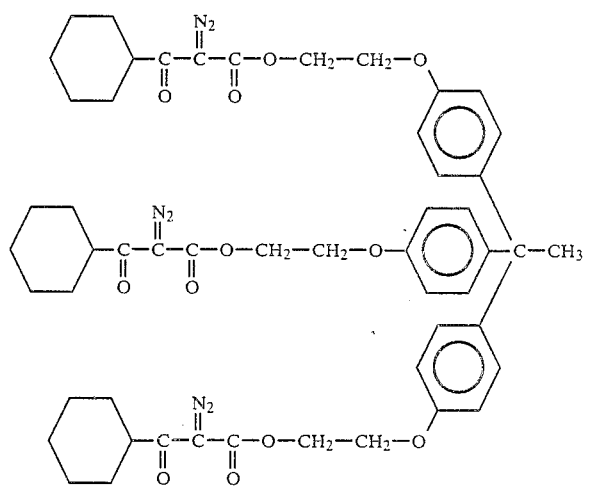
Compound (18)
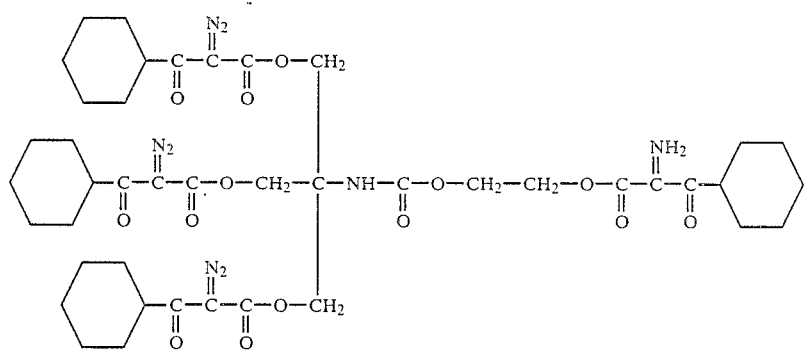
Compound (20)
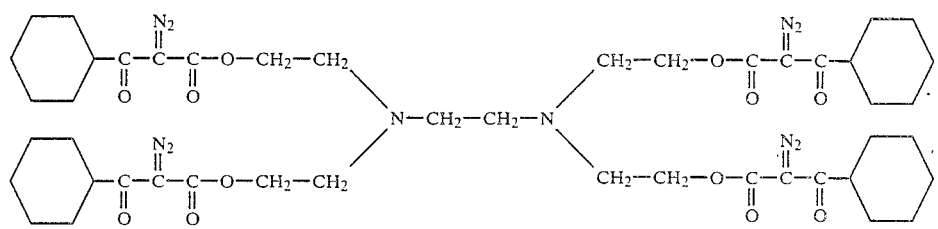
Compound (22)

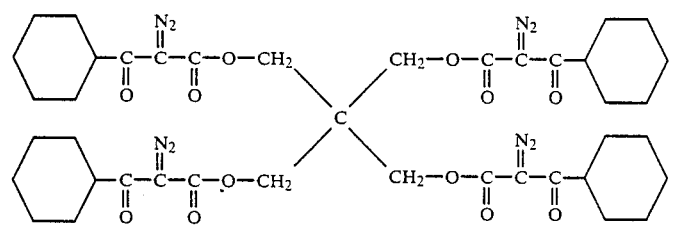

Compound (25)

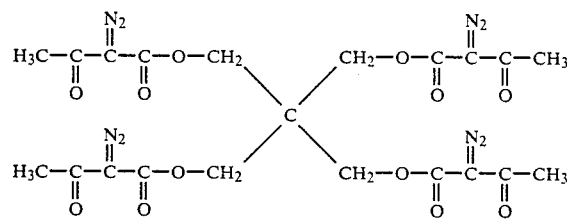

Comparison compound (26)

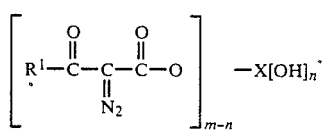

What is claimed is:

1. A polyfunctional α-diazo-β-keto ester which has the general formula I $$\left[ R^1 - \underset{\underset{N_2}{\|}}{C} - \underset{O}{\overset{O}{\|}}{C} - \underset{O}{\overset{O}{\|}}{C} - O \right]_{m-n} - X[OH]_n \quad (I)$$

in which
R¹ denotes an aliphatic, cycloaliphatic or aralphatic or aromatic radical having 4 to 20 carbon atoms, in which individual CH₂ groups can be replaced by divalent atoms or divalent groups selected from the group consisting of oxygen, sulfur, NH and carbonyl, and individual CH groups can be replaced by -N-,
X denotes an at least divalent aliphatic, cycloaliphatic, carbocyclic, heterocyclic or aralphatic radical having 2 to 22 carbon atoms, in which individual CH₂ groups can be replaced by oxygen or sulfur atoms or by the groups

—NR²—, —C(O)— O—, —C(O)—NR²—,

—NR²—C(O)—NR³—, —O— C(O)—NR²—,

—O—C(O)—O— or

CH groups can be replaced by —C(O)—N—, —O—C(O)—N— or —N— in which R² and R³ independently of one another represent hydrogen or an aliphatic, carbocyclic or aralphatic radical having 1 to 15 carbon atoms,
m denotes an integer from 2 to 10 and
n denotes an integer from 0 to 2,
wherein
m−n is ≧2.

2. A polyfunctional α-diazo-β-keto ester as claimed in claim 1, in which R₂ and R₃ denote hydrogen, (C₁-C₃)alkyl, (C₆-C₁₂)aryl or (C₆-C₁₁)aralkyl.

3. A polyfunctional α-diazo-β-keto ester as claimed in claim 2, wherein said (C₁-C₃)alkyl, (C₆-C₁₂)aryl or (C₆-C₁₁)aralkyl groups are further substituted by (C₁-C₃)alkyl, (C₁-C₃)alkoxy, halogen or amino.

4. A polyfunctional α-diazo-β-keto ester as claimed in claim 1, in which R¹ or X are substituted by (C₁-C₃)alkyl, (C₁-C₃)alkoxy, halogen, amino or nitro.

5. A polyfunctional α-diazo-β-keto ester as claimed in claim 1, in which R¹ is a substituted aliphatic radical having 4 to 10 chain members.

6. A polyfunctional α-diazo-β-keto ester as claimed in claim 5, in which up to 3 CH₂ groups are replaced by oxygen atoms, —NH— groups or keto groups and these radicals therefore contain ether, keto, ester, amido or imido groups.

7. A polyfunctional α-diazo-β-keto ester as claimed in claim 1, in which $R^1$ is an unsubstituted aliphatic radical containing up to 20 chain members.

8. A polyfunctional α-diazo-β-keto ester as claimed in claim 7, in which $R^1$ is a t-butyl radical.

9. A polyfunctional α-diazo-β-keto ester as claimed in claim 1, in which $R^1$ denotes a substituted or unsubstituted cycloaliphatic radical having 4, 5, 6 or 12 ring members.

10. A polyfunctional α-diazo-β-keto ester as claimed in claim 9, in which $R^1$ has 4, 5 or 6 ring members.

11. A polyfunctional α-diazo-β-keto ester as claimed in claim 10, in which $R^1$ has 6 ring members.

12. A polyfunctional α-diazo-β-keto ester as claimed in claim 9, in which $R^1$ is unsubstituted.

13. A polyfunctional α-diazo-β-keto ester as claimed in claim 1, in which $R^1$ is an araliphatic radical having 2 to chain members in the aliphatic part of the radical.

14. A polyfunctional α-diazo-β-keto ester as claimed in claim 13, in which $R^1$ has 2 to 5 chain members in the aliphatic part of the radical.

15. A polyfunctional α-diazo-β-keto ester as claimed in claim 13, in which the aliphatic part of the radical $R^1$ is a pure carbon chain containing 1 or 2 chain members.

16. A polyfunctional α-diazo-β-keto ester as claimed in claim 13, in which the aliphatic part of the radical $R^1$ contains 2 to 5 chain members, wherein up to 3 $CH_2$ groups in this part are replaced by hetero atoms.

17. A polyfunctional α-diazo-β-keto ester as claimed in claim 1, in which not more than 5 $CH_2$ and CH groups in the radical X are replaced by the recited hetero atoms or groups.

18. A polyfunctional α-diazo-β-keto ester as claimed in claim 17, in which not more than 3 $CH_2$ and CH groups in the radical X are replaced by the recited hetero atoms or groups.

19. A polyfunctional α-diazo-β-keto ester as claimed in claim 1, in which the radical X is aliphatic and unsubstituted and contains not more than 6 carbon atoms.

20. A polyfunctional α-diazo-β-keto ester as claimed in claim 19, in which this radical contains not more than one carbon-carbon double or triple bond.

21. A polyfunctional α-diazo-β-keto ester as claimed in claim 17, in which the hetero atoms replacing $CH_2$ groups are of one type.

22. A polyfunctional α-diazo-β-keto ester as claimed in claim 17, in which a CH group is replaced by

and no further substitution is present in the radical X.

23. A polyfunctional α-diazo-β-keto ester as claimed in claim 17, in which X is a cycloaliphatic radical in which the cycloaliphatic part is unsubstituted and is adjacent to a $CH_2$ group of the aliphatic part, which is replaced by at least one of the recited hetero atoms or by groups.

24. A polyfunctional α-diazo-β-keto ester as claimed in claim 23, in which the cycloaliphatic part is directly adjacent to a nitrogen atom.

25. A polyfunctional α-diazo-β-keto ester as claimed in claim 24, wherein the cycloaliphatic part is directly adjacent to the

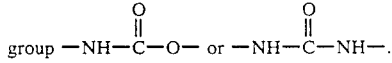

26. A polyfunctional α-diazo-β-keto ester as claimed in claim 23, in which the cycloaliphatic part is linked via an ethylene group to the oxygen atom of a

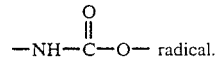

27. A polyfunctional α-diazo-β-keto ester as claimed in claim 17, in which X is an araliphatic radical.

28. A polyfunctional α-diazo-β-keto ester as claimed in claim 27, in which the aromatic part is a phenyl or phenylene radical which is linked via a hetero atom to the aliphatic part of the radical.

29. A polyfunctional α-diazo-β-keto ester as claimed in claim 1, in which m is an integer from 2 to 8 and n is an integer from 0 to 2.

30. A polyfunctional α-diazo-β-keto ester as claimed in claim 29, in which m is an integer from 2 to 6 and n is 0.

* * * * *

UNITED STATES PATENT AND TRADEMARK OFFICE
CERTIFICATE OF CORRECTION

PATENT NO. : 4,996,301
DATED : February 26, 1991
INVENTOR(S) : Peter WILHARM, et al.

It is certified that error appears in the above—identified patent and that said Letters Patent is hereby corrected as shown below:

Claim 1, Column 30, lines 42 and 43 change "CH groups can be replaced by -C(O)-N-,-O-C(O)-N- or - N-" to -- -CH groups can be replaced by -C(O)-N-, -O-C(O)-N- or -N- --.
Claim 13, Column 31, line 22, after "to" insert --11--.

Signed and Sealed this

Seventeenth Day of November, 1992

Attest:

DOUGLAS B. COMER

Attesting Officer   Acting Commissioner of Patents and Trademarks